US008212132B2

(12) United States Patent
Swager et al.

(10) Patent No.: US 8,212,132 B2
(45) Date of Patent: Jul. 3, 2012

(54) FUNCTIONALIZATION OF NANOSCALE ARTICLES INCLUDING NANOTUBES AND FULLERENES (75) Inventors: Timothy M. Swager, Newton, MA (US); Wei Zhang, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 847 days.

(21) Appl. No.: 12/044,854

(22) Filed: Mar. 7, 2008

(65) Prior Publication Data

US 2008/0221240 A1 Sep. 11, 2008

Related U.S. Application Data (60) Provisional application No. 60/905,495, filed on Mar. 7, 2007.

(51) Int. Cl.
*B82Y 40/00* (2011.01)
*B82Y 30/00* (2011.01)
*B82Y 15/00* (2011.01)
(52) U.S. Cl. .................. 977/847; 977/745; 977/746
(58) Field of Classification Search .............. 977/847, 977/745, 746
See application file for complete search history.

(56) References Cited

U.S. PATENT DOCUMENTS

| 6,616,497 | B1 | 9/2003 | Choi et al. |
| 6,705,910 | B2 | 3/2004 | Sheu et al. |
| 6,902,658 | B2 | 6/2005 | Talin et al. |
| 7,014,743 | B2 | 3/2006 | Zhou et al. |
| 7,187,115 | B2 | 3/2007 | Seon |
| 2002/0037457 | A1 | 3/2002 | Choi |
| 2006/0057927 | A1 | 3/2006 | Kang et al. |
| 2006/0063464 | A1 | 3/2006 | Kang et al. |
| 2008/0076816 | A1 | 3/2008 | Bianco et al. |
| 2008/0131658 | A1 | 6/2008 | Wakharkar et al. |
| 2010/0179054 | A1 | 7/2010 | Swager et al. |
| 2011/0081724 | A1 | 4/2011 | Swager et al. |
| 2011/0089051 | A1 | 4/2011 | Wang et al. |
| 2011/0171629 | A1 | 7/2011 | Swager et al. |

FOREIGN PATENT DOCUMENTS

| CN | 1995143 A | 7/2007 |
| JP | 2008-047855 A | 2/2008 |
| WO | WO 01/10779 A1 | 2/2001 |
| WO | WO 2004/113275 A2 | 12/2004 |
| WO | WO 2006/115486 A1 | 11/2006 |
| WO | WO 2007/033189 A1 | 3/2007 |
| WO | WO 2007/098578 A1 | 9/2007 |
| WO | WO 2008/133779 A2 | 11/2008 |
| WO | WO 2009/136978 A2 | 11/2009 |

OTHER PUBLICATIONS

Diederich, F. et al., Science, 1996, vol. 271, pp. 317-323.*
Shu, L. et al., Chem. Commun., 1997, 79-80.*
O'Donovan, B. Chem. Commun., 1997, 81-82.*
Sun, Y.-P. et al., Acc. Chem. Res. 2002, vol. 35, pp. 1096-1104.*
Prato, M. Acc. Chem. Res. 1998, vol. 31, pp. 519-526.*
Silverman, R. "The Organic Chemistry of Drug Design and Drug Action," 2004, Elsevier, pp. 29-32.*
Zhou, Z. et al., Org. Lett., 2005, vol. 7, pp. 5849-5851.*
Baughman, R. et al., "Carbon Nanotubes—The Route Toward Applications," *Science*, 2002, 297(2), 787-792.
Becker, H. et al., "The Influence of Surface Strain on the Chemical Reactivity of Fullerene Ions: Addition Reactions with Cyclopentadiene and 1,3-cycolhexadiene," *International Journal of Mass Spectrometry and Ion Processes*, 1997, 167/168, 519-524.
Chen, J. et al., "Dissolution of Full-Length Single-Walled Carbon Nanotubes," *J. Phys. Chem. B*, 2001, 105, 2525-2528.
Khare, R. et al., "Carbon Nanotube Based Composites—A Review," *Journal of Minerals & Materials Characterization & Engineering*, 2005, 4(1), 31-46.
Preda, D. et al., "Addition of Dihalocarbenes to Corannulene. A Fullerene-Type Reaction," *Tetrahedron Letters*, 2000, 41, 9633-9637.
Scott, L. "Fragments of Fullerenes: Novel Syntheses, Structures and Reactions," *Pure & Appl. Chem.*, 1996, 68(2), 291-300.
Serp, P. et al., "Carbon Nanotubes and Nanofibers in Catalysis," *Applied Catalysis A: General*, 2003, 253, 337-358.
Tasis, D. et al., "Chemistry of Nanotubes," *Chem. Rev.*, 2006, 106, 1105-1136.
Wei, Z. et al., "Covalent functionalization of single walled carbon nanotubes and fullerences via a switterion approach," *Chemical Abstracts*, 2 pages.
Zhang, W. et al., "Covalent Functionalization of Singled Walled Carbon Nanotubes and Fullerenes via a Zwitterion Approach," *Prep. Pap.-Am. Chem. Soc., Div. Fuel. Chem.*, 2007, 52(1), 126-128.
Zhou, Z. et al., "A New Method for the Functionalization of [60] Fullerene: An Unusual 1,3-Dipolar Cycloaddition Pathway Leading to a $C_{60}$ Housane Derivative," *Organic Letters*, 2005, 7(26), 5849-5851.
International Search Report and Written Opinion from International Patent Application Serial No. PCT/US2008/003180, filed Mar. 7, 2008, mailed Jun. 19, 2009.
International Preliminary Report on Patentability from International Patent Application Serial No. PCT/US2008/003180, date of issuance Sep. 8, 2009.
Maggini, M. et al., "Addition of Azomethine Ylides to $C_{60}$: Synthesis, Characterization, and Functionalization of Fullerene Pyrrolidines," *J. Am. Chem. Soc.* 1993, 115, 9798-9799.

(Continued)

*Primary Examiner* — Janet Andres
*Assistant Examiner* — Heidi Reese
(74) *Attorney, Agent, or Firm* — Wolf, Greenfield & Sacks, P.C.

(57) ABSTRACT

The present invention generally provides compositions including carbon-containing molecules, and related methods. In some cases, the present invention relates to aromatic molecules comprising functional groups bonded to the aromatic portion of the molecule, including nonplanar portions of the molecules. Methods of the invention may provide the ability to introduce a wide range of functional groups to carbon-containing molecules. In some cases, methods of the invention may be performed using relatively mild reaction conditions, such as relatively low temperature, low pressure, and/or in the absence of strong acids or strong bases. The present invention may provide a facile and modular approach to synthesizing molecules that may be useful in various applications including photovoltaic devices, sensors, and electrodes (e.g., for electrocatalysis).

6 Claims, 4 Drawing Sheets

OTHER PUBLICATIONS

Wang, Guan-Wu et al., "Novel multicomponent reaction of [60]fullerene: the first example of 1,4-dipolar cycloaddition reaction in fullerene chemistry," *Org. Biomol. Chem.*, 2006, 4, 4063-4064.

Invitation to Pay Additional Fees for PCT/US2009/001396 mailed Dec. 10, 2009.

International Search Report and Written Opinion for PCT/US2009/001396 mailed Apr. 22, 2010.

International Preliminary Report on Patentability for PCT/US2009/001396 mailed Sep. 16, 2010.

International Search Report and Written Opinion for PCT/US2009/006512 mailed Oct. 22, 2010.

International Preliminary Report on Patentability for PCT/US2009/006512 mailed Jun. 23, 2011.

[No Author Listed] TGP—H Carbon Fiber Paper. Toray Automotive Solutions. Toray Industries (America), Inc. Available at http://www.toray-auto.us/poductrs/carbon_papers_fuel_cells.html. Last accessed Nov. 19, 2010. 2 pages.

Albert et al., Cross-reactive chemical sensor arrays. Chem Rev. Jul. 12, 2000;100(7):2595-626.

Bai et al., Gas Sensors Based on Conducting Polymers. Sensors. 2007;7:267-307.

Chen et al., Noncovalent functionalization of carbon nanotubes for highly specific electronic biosensors. Proc Natl Acad Sci U S A. Apr. 29, 2003;100(9):4984-9. Epub Apr. 15, 2003.

Coffey et al., Conducting Polymer/Graphite Fiber Composites for High Charge Density Battery Electrodes. Lithium batteries—Symposium. Proceedings—Electrochemical Society. New Orleans, LA. Oct. 1993. The Society. 1994;94-4:258-68.

Coffey et al., High charge density conducting polymer/graphite fiber composite electrodes for battery applications. J Electrochem Soc. 1995;142(2):321-25.

Collins et al., Extreme oxygen sensitivity of electronic properties of carbon nanotubes. Science. Mar. 10, 2000;287(5459):1801-4.

Janata et al., Conducting polymers in electronic chemical sensors. Nat Mater. Jan. 2003;2(1):19-24.

Kamat et al., Self-Assembled Linear Bundles of Single Wall Carbon Nanotubes and Their Alignment and Deposition as a Film in a dc Field. J Am Chem Soc. 2004;126(34):10757-62.

Kolmakov et al., Chemical Sensing and Catalysis by One-Deminsional Metal-Oxide Nanostructures. Annu Rev Mater Res. 2004;34:151-80.

Kong et al., Nanotube molecular wires as chemical sensors. Science. Jan. 28, 2000;287(5453):622-5.

Lobez et al., Radiation Detection: Resistivity Responses in Functional Poly (Olefin Sulfone)/Carbon Nanotube Composites. Angew Chem Int Ed. 2010; 49:95-98.

Lutz, 1,3-Dipolar cycloadditions of azides and alkynes: a universal ligation tool in polymer and materials science. Angew Chem Int Ed. 2007; 46:1018-25.

McQuade et al., Conjugated Polymer-Based Chemical Sensors. Chem Rev. 2000;100:2537-74.

Moses et al., The growing applications of click chemistry. Chem Soc Rev. Aug. 2007;36(8):1249-62. Epub May 3, 2007.

Park et al., Enhancement of the field-effect mobility of poly(3-hexylthiophene)/functionalized carbon nanotube hybrid transistors. Org Electon. 2008;9:317-22.

Potyrailo, Polymeric Sensoir Materials: Toward an Alliance of Combinatorial and Rational Design Tools? Agnew Chem Int Ed. 2006;45:702-23.

Qi et al., Toward Large Arrays of Multiplex Functionalized Carbon Nanotube Sensors for Highly Sensitive and Selective Molecular Detection. Nano Lett. 2003;3(3):347-51.

Rostovtsev et al., A stepwise huisgen cycloaddition process: copper(I)-catalyzed regioselective "ligation" of azides and terminal alkynes. Angew Chem Int Ed Engl. Jul. 15, 2002;41(14):2596-9.

Santhanam et al., A chemical sensor for chloromethanes using a nanocomposite of multiwalled carbon nanotubes with poly(3-methylthiophene). Sensors and Actuators B. 2005;106:766-71.

Snow et al., Chemical detection with a single-walled carbon nanotube capacitor. Science. Mar. 25, 2005;307(5717):1942-5.

Star et al., Electronic Detection of Specific Protein Binding Using Nanotube FET Devices. Nano Lett. 2003;3(4):459-63.

Star et al., Nanoelectronic Carbon Dioxide Sensors. Adv Mater. 2004;16(22):2049-52.

Swager, The Molecular Wire Approach to Sensory Signal Amplificiation. Acc Chem Res. 1998;31:201-07.

Toal et al., Polymer sensors for niroaromatic explosives detection. Mater Chem. 2006;16:2871-83.

Tombler et al., Reversible electromechanical characteristics of carbon nanotubes under local-probe manipulation. Nature. 2000;405:769-72.

Wang et al., Carbon Nanotube/Polythiophene Chemiresistive Sensors for Chemical Warfare Agents. J Am Chem Soc. 2008;130:5392-93.

Wei et al., Multifunctional chemical vapor sensors of aligned carbon nanotube and polymer composites. J Am Chem Soc. Feb. 8, 2006;128(5):1412-3.

Weizmann et al., DNA-CNT nanowire networks for DNA detection. J Am Chem Soc. Mar. 16, 2011;133(10):3238-41. Epub Feb. 22, 2011.

Zhang et al., Electochemically Functionalized Single-Walled Carbon Nanotube Gas Sensor. Electroanalysis. 2006;18(12):1153-58.

Zhang et al., Functionalization of single-walled carbon nanotubes and fullerenes via a dimethyl acetylenedicarboxylate-4-dimethylaminopyridine zwitterion approach. J Am Chem Soc. Jun. 27, 2007;129(25):7714-5. Epub Jun. 2, 2007.

Zhang et al., Modular Functionalization of Carbon Nanotubes and Fullerenes. J Am Chem Soc. 2009;131:8446-54.

\* cited by examiner

FUNCTIONALIZATION OF NANOSCALE ARTICLES INCLUDING NANOTUBES AND FULLERENES

RELATED APPLICATIONS

This application claims priority under 35 U.S.C. §119(e) to co-pending U.S. Provisional Application Ser. No. 60/905,495, filed Mar. 7, 2007, the contents of which are incorporated herein by reference.

FIELD OF THE INVENTION

The present invention provides compositions including substituted carbon-containing molecules, and related methods.

BACKGROUND OF THE INVENTION

Nonplanar carbon-containing molecules such as carbon nanotubes and fullerenes have attracted great attention due to their unique mechanical and electronic properties, as well as their potential applications in nanotechnology. Typically, such molecules are obtained by high temperature methods including graphite vaporization and arc vaporization. Also, the molecules generally have low solubility. Covalent functionalization of carbon nanotubes may often be desired to optimize their properties. However, only a few methods have been developed for this purpose, including the addition of carbenes, nitrenes, or diazonium salts to the surface of the carbon nanotubes. Also, functionalization of carbon nanotubes may be achieved via 1,3-dipolar cycloaddition of azomethine ylides. However, many of the known methods require high temperatures, long reaction times, and/or a strong base or strong acid.

Accordingly, improved methods are needed.

SUMMARY OF THE INVENTION

The present invention relates to compositions comprising a compound having the formula, wherein: A is a carbon-containing molecule comprising a nonplanar aromatic portion; $R^1$, $R^2$, and $R^3$ can be the same or different and are =O, hydroxy, halide, alkyl, heteroalkyl, alkenyl, heteroalkenyl, alkynyl, heteroalkynyl, aryl, or heteroaryl, optionally substituted; and === is a single bond or double bond.

The present invention also relates to compositions comprising a compound having the formula, wherein: A is a carbon-containing molecule comprising a nonplanar aromatic portion; $R^1$, $R^2$, and $R^3$ can be the same or different and each is an atom or a chemical group, wherein at least one of $R^1$, $R^2$, and $R^3$ can be replaced with a second atom or chemical group or can participate in linkage to a second atom or chemical group under conditions unreactive to the remainder of the compound other than $R^1$, $R^2$, or $R^3$; and === is a single bond or double bond.

The present invention also relates to compositions comprising a fused network of aromatic rings, optionally comprising a border at which the fused network terminates, and a functional group comprising a five-membered carbon ring fused to the network via two atoms, wherein the two atoms are ring atoms of at least two aromatic rings of the network.

The present invention also provides methods for synthesizing a substituted carbon-containing molecule, comprising reacting an alkyne, a carbon-containing molecule comprising a nonplanar aromatic portion, and a nucleophile having a $pK_a$ more positive than 5.0 to form a substituted carbon-containing molecule, wherein the nucleophile has a conjugate acid having a $pK_a$ more positive than 5.0.

The present invention also provides methods for synthesizing a substituted carbon-containing molecule, comprising reacting an alkyne, a carbon-containing molecule, and a nucleophile at a temperature less than 100° C. and at a pressure of less than 10,000 atm, to form a product, wherein the product is a substituted carbon-containing molecule comprising a fused network of aromatic rings and a functional group comprising a ring comprising at least four ring atoms, wherein the functional group is fused to the network via two atoms, wherein the two atoms are ring atoms of at least two aromatic rings of the network.

Other aspects, embodiments and features of the invention will become apparent from the following detailed description when considered in conjunction with the accompanying drawings. The accompanying figures are schematic and are not intended to be drawn to scale. For purposes of clarity, not every component is labeled in every figure, nor is every component of each embodiment of the invention shown where illustration is not necessary to allow those of ordinary skill in the art to understand the invention. All patent applications and patents incorporated herein by reference are incorporated by reference in their entirety. In case of conflict, the present specification, including definitions, will control.

DETAILED DESCRIPTION

The present invention generally provides compositions including carbon-containing molecules, and related methods.

In some cases, the present invention relates to aromatic molecules comprising functional groups bonded to the aromatic portion of the molecule, including nonplanar portions of the molecule, and methods of synthesizing such molecules. Methods of the invention may advantageously provide the ability to introduce a wide range of functional groups to aromatic molecules, including carbon-containing molecules. In some cases, methods of the invention may be performed using relatively mild reaction conditions, such as relatively low temperature, low pressure, and/or in the absence of strong acids or strong bases. The present invention may provide a facile and modular approach to synthesizing molecules that may be useful in various applications including photovoltaic devices, sensors, batteries, and electrodes (e.g., for electrocatalysis).

In some embodiments, the present invention provides methods for synthesizing substituted or functionalized carbon-containing molecules. As used herein, the terms "substituted" and "functionalized" are given their ordinary meaning in the art and refer to species which have been altered (e.g., reacted) such that a new functional group (e.g., atom or chemical group) is bonded to the species. In some cases, the functional group may form a bond to at least one atom of a carbon-containing molecule. In some cases, the functional group may replace another group already bonded to the carbon-containing molecule such as, for example, a hydrogen atom. In some cases, the functional group (e.g., a ring) may be fused to the carbon-containing molecule via at least two atoms of the carbon-containing molecule. Methods of the invention may allow for functionalization of carbon-containing molecules using a wide range of atoms or chemical groups. In some cases, the present invention may allow for functionalization of multiple groups and/or functionalization at selected locations on the carbon-containing molecule.

Some embodiments of the invention may comprise the synthesis of a carbon-containing molecule comprising a functional group fused to the aromatic portion of the molecule. The functional group may include atoms or groups which may be further reacted to attach additional groups to the carbon-containing molecule and/or functional group. That is, the functional group may serve as a precursor for a wide range of additional functional groups that may be bonded to the carbon-containing molecule. This may allow for the facile tailoring of various properties of carbon-containing molecules, including stability, solubility, miscibility, biocompatibility, optical properties, electronic properties, binding properties, surface affinities, and the like.

Carbon-containing molecules, as described herein, may typically comprise a fused network of rings, such as aromatic rings. In some embodiments, the carbon-containing molecule comprises a fused network of at least 10, at least 20, at least 30, at least 40, or, in some cases, at least 50 aromatic rings. The carbon-containing molecule may be substantially planar or substantially non-planar, or may comprise a planar or non-planar portion. The carbon-containing molecule may optionally comprise a border at which the fused network terminates. For example, a sheet of graphite is a planar carbon-containing molecule comprising a border at which the fused network terminates, while a fullerene is a nonplanar carbon-containing molecule which lacks such a border. In some cases, the border may be substituted with hydrogen atoms. In some cases, the border may be substituted with groups comprising oxygen atoms (e.g., hydroxyl). In other cases, the border may be substituted as described herein. The term "fused network" might not include, for example, a biphenyl group, wherein two phenyl rings are joined by a single bond and are not fused. In some cases, the fused network may substantially comprise carbon atoms. In some cases, the fused network may comprise carbon atoms and heteroatoms. Some examples of carbon-containing molecules include graphene, carbon nanotubes (e.g., single-walled carbon nanotubes, multi-walled carbon nanotubes), and fullerenes.

The carbon-containing molecule may optionally comprise a nonplanar portion, e.g., a curved portion having a convex surface and a concave surface (where "surface," in this context, defines a side of a molecule or sheet defining a polycyclic structure). Examples of carbon-containing molecules comprising non-planar portions include fullerenes, carbon nanotubes, and fragments thereof, such as corannulene. In some cases, the nonplanar aromatic portion may comprise carbon atoms having a hybridization of $sp^{2-x}$, wherein x is between 1 and 9, i.e., the carbon atom may have a hybridization between $sp^2$- and $sp^3$-hybridization, where this hybridization is characteristic of non-planarity of the molecule as would be understood by those of ordinary skill in the art. In these embodiments, x can also be between 2 and 8, between 3 and 7, or between 4 and 6. Typically, planar aromatic groups and polycyclic aromatic groups (e.g., phenyl, naphthyl) may comprise carbon atoms having $sp^2$ hybridization, while non-aromatic, non-planar groups (e.g., alkyl groups) may comprise carbon atoms having $sp^3$ hybridization. For carbon atoms in a non-planar aromatic group, such as a nonplanar portion of a carbon-containing molecule, $sp^2$-hybridized carbon atoms may be distorted (e.g., bent) to form the nonplanar or curved portion of a carbon-containing molecule. Without wishing to be bound by theory, this distortion may cause angle strain and may alter the hybridization of the carbon atoms. As a result, the reactivity of the strained carbon atoms may be enhanced.

In some cases, the carbon-containing molecule is a fullerene. As used herein, the term "fullerene" is given its ordinary meaning in the art and refers to a substantially spherical molecule generally comprising a fused network of five-membered and/or six-membered aromatic rings. For example, $C_{60}$ is a fullerene which mimics the shape of a soccer ball. The term fullerene may also include molecules having a shape that is related to a spherical shape, such as an ellipsoid. It should be understood that the fullerene may comprise rings other than six-membered rings. In some embodiments, the fullerene may comprise seven-membered rings, or larger. Fullerenes may include $C_{36}$, $C_{50}$, $C_{60}$, $C_{70}$, $C_{76}$, $C_{84}$, and the like.

In some cases, the carbon-containing molecule is a carbon nanotube. As used herein, the term "carbon nanotube" is given its ordinary meaning in the art and refers to a substantially cylindrical molecule comprising a fused network of six-membered aromatic rings. In some cases, carbon nanotubes may resemble a sheet of graphite rolled up into a seamless cylindrical structure. It should be understood that the carbon nanotube may also comprise rings other than six-membered rings. Typically, at least one end of the carbon nanotube may be capped, i.e., with a curved or nonplanar aromatic group. Carbon nanotubes may have a diameter of the order of nanometers and a length on the order of millimeters, resulting in an aspect ratio greater than 100, 1000, 10,000, or greater. The term "carbon nanotube" includes single-walled nanotubes (SWCNTs), multi-walled nanotubes (MWCNTs) (e.g., concentric carbon nanotubes), inorganic derivatives thereof, and the like. In some embodiments, the carbon nanotube is a single-walled carbon nanotube. In some cases, the carbon nanotube is a multi-walled carbon nanotube (e.g., a double-walled carbon nanotube).

The present invention provides compositions comprising carbon-containing molecules and a functional group bonded thereto. For example, the composition may comprise a fused network of aromatic rings, optionally comprising a border at which the fused network terminates, and a functional group comprising a five-membered carbon ring fused to the network via two atoms, wherein the two atoms are ring atoms of at least two aromatic rings of the network. In some embodiments, the present invention provides compositions comprising compounds having the formula, wherein A is a carbon-containing molecule comprising a nonplanar aromatic portion; $R^1$, $R^2$, and $R^3$ can be the same or different and each is an atom or a chemical group; and === is a single bond or double bond. In some cases, $R^1$, $R^2$, and $R^3$ can be =O, hydroxy, halide, alkyl, heteroalkyl, alkenyl, heteroalkenyl, alkynyl, heteroalkynyl, aryl, or heteroaryl, optionally substituted. In the structure above, the five membered carbon ring may be fused to A via two atoms of A, such that the structure comprises a group wherein "∼∼∼" comprises the nonplanar aromatic portion. The two atoms may be ring atoms of at least two aromatic rings of the fused network. In some embodiments, the compound may comprise the structure, wherein $R^1$ is an ester and $R^2$ is a leaving group. $R^1$ may be an acid chloride, carboxylic acid or salt thereof, ester, amide, or substituted derivative thereof.

In some embodiments, $R^1$ has the structure, wherein X is H, OH, halide, alkyl, heteroalkyl, alkenyl, heteroalkenyl, alkynyl, heteroalkynyl, aryl, heteroaryl, or salt thereof, optionally substituted; $R^2$ is a leaving group; and $R^3$ is =O, =S, or =NR$^4$. $R^1$ can be an acid chloride, carboxylic acid or salt thereof, ester, amide, other carbonyl groups or substituted derivative thereof. As used herein, a "leaving group" is given its ordinary meaning in the art of synthetic organic chemistry and refers to an atom or a group capable of being displaced by a nucleophile. Examples of suitable leaving groups include, but are not limited to, halides (such as chloride, bromide, and iodide), alkanesulfonyloxy, arenesulfonyloxy, alkyl-carbonyloxy (e.g., acetoxy), arylcarbonyloxy, mesyloxy, tosyloxy, trifluoromethane-sulfonyloxy, aryloxy, methoxy, N,O-dimethylhydroxylamino, pixyl, and the like. In some cases, the leaving group is an aryloxy group substituted with an electron-withdrawing group (e.g., 2, -nitrophenoxy, 2,4-dinitrophenoxy). Some specific examples of leaving groups include the structures, In one embodiment, the compound may have the structure,

In some embodiments, the compound may have the structure, wherein $R^5$ is alkyl, heteroalkyl, alkenyl, heteroalkenyl, alkynyl, heteroalkynyl, aryl, heteroaryl, or a salt thereof, optionally substituted.

In some embodiments, $R^1$, $R^2$, and/or $R^3$ may be joined to form a ring. For example, any two of $R^1$, $R^2$, and $R^3$ may be joined to form a ring. The ring may comprise any number of ring atoms and may include carbon atoms, heteroatoms, metals, and the like. The ring may also be optionally substituted, as described herein. In some embodiments, $R^1$ and $R^3$ may be joined to form a ring comprising at least six ring atoms.

Figure 4:
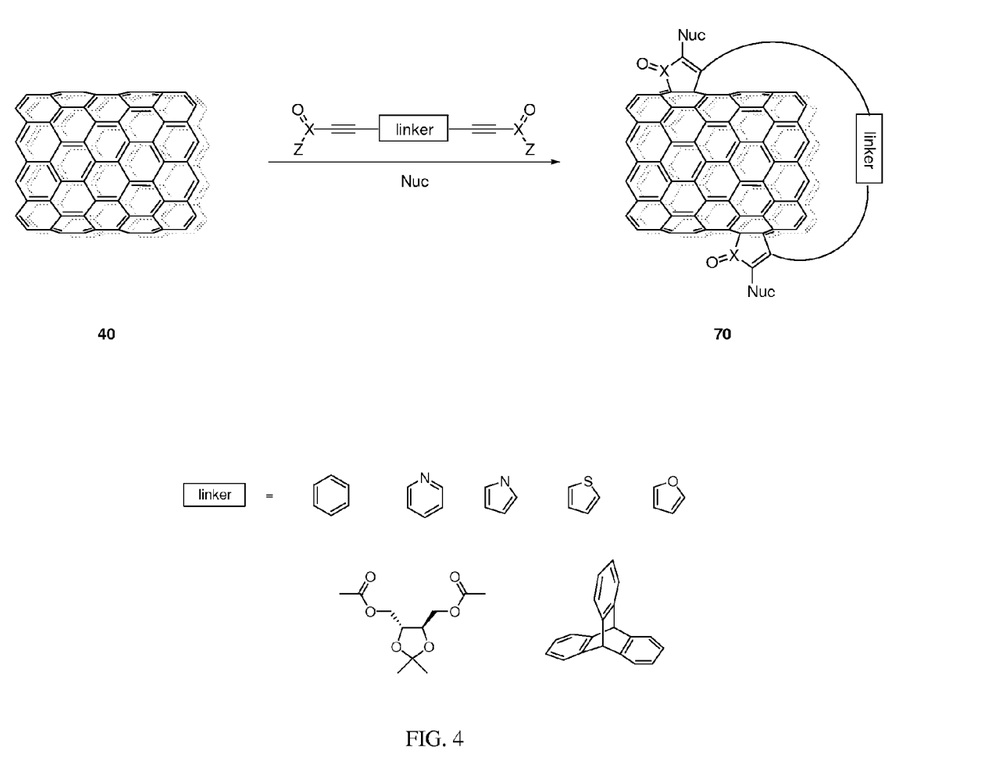
FIG. 4 shows a synthesis of a multi-functionalized carbon nanotube comprising two functional groups joined by a linker, according to one embodiment of the invention.

Some embodiments of the invention may comprise at least two or more functional groups fused to the carbon-containing molecule. In some cases, the two or more functional groups may be joined by a linker. The carbon-containing molecule may comprise at least two groups having the formula, wherein $R^1$ of each functional group is joined by a linker. The linker may be a flexible linker such as an alkyl or heteroalkyl group, or the linker may be a rigid linker, such as an aryl, heteroaryl, alkene, heteroalkene, alkyne, or heteroalkyne group. For example, the linker may be a phenyl, pyridinyl, pyrrolyl, thiophenyl, furanyl, biphenyl, or iptycenyl group, a tartrate ester, an acetylene, an alkene, combinations thereof, or the like. In some cases, the linker may be covalently bonded to the functional groups. In some cases, the linker may be non-covalently bonded to the functional groups. Examples of non-covalent bonds include ionic bonds, hydrogen bonds (e.g., between hydroxyl, amine, carboxyl, thiol and/or similar functional groups, for example), dative bonds (e.g. complexation or chelation between metal ions and monodentate or multidentate ligands), or the like. Non-covalent bonds may also comprise Van der Waals interactions. As shown by the illustrative embodiment in FIG. 4, compound 70 is a carbon nanotube comprising two, five-membered rings, each fused to a different nonplanar portion of the carbon nanotube, wherein the two rings are joined by a linker.

Figure 1:
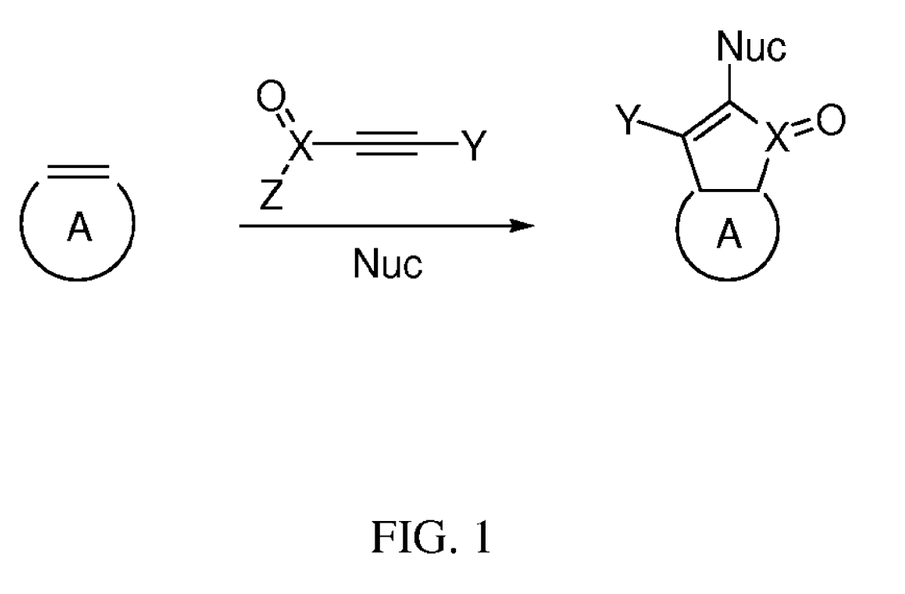
FIG. 1 shows a synthesis of a functionalized carbon-containing molecule, according to one embodiment of the invention.

The present invention also provides methods for synthesizing functionalized or substituted carbon-containing molecules. Some embodiments may comprise reacting an alkyne, a carbon-containing molecule, and a nucleophile to produce a substituted carbon-containing molecule. As shown by the illustrative embodiment in FIG. 1, the alkyne, carbon-containing molecule, and nucleophile may react to form a product comprising at least a portion of each component (e.g., alkyne, carbon-containing molecule, and nucleophile) covalently bound to one another. As used herein, the term "react" or "reacting" refers to the formation of a bond between two or more components to produce a stable, isolable compound. For example, a first component and a second component may react to form one reaction product comprising the first component and the second component joined by a covalent bond. That is, the term "reacting" does not refer to the interaction of solvents, catalysts, bases, ligands, or other materials which may serve to promote the occurrence of the reaction with the component(s). A "stable, isolable compound" refers to isolated reaction products and does not refer to unstable intermediates or transition states. A variety of functional groups may be installed on the carbon-containing molecule by varying the alkyne (e.g., electrophile) and nucleophile.

In some embodiments, the carbon-containing molecule may comprise a nonplanar aromatic portion, such that reaction with an alkyne and nucleophile results in the formation of a functional group bonded to the nonplanar aromatic portion of the carbon-containing molecule. For example, the functional group may comprise a ring fused to the carbon-containing molecule via two atoms of the nonplanar aromatic portion. The ring may comprise carbon atoms, or a combination of carbon atoms and heteroatoms. In some cases, the ring may comprise at least four ring atoms, at least five ring atoms, at least six ring atoms, or more. In some embodiments, a five membered ring may be fused to the carbon-containing molecule.

In some cases, two or more functional groups or precursors thereof (e.g., alkyne, nucleophile) may be joined by a linker, as described herein. For example, the method may comprise the formation of at least two functional groups fused to a carbon-containing molecule, wherein the at least two functional groups are joined by a linker group. The linker may be, for example, a tartrate ester, an aromatic group, or other groups as described herein. In some cases, the carbon-containing molecule may be functionalized at one or more locations on the carbon-containing molecule, wherein the relative position of the locations may be selected by choosing a linker of the appropriate size and/or length. For example, formation of two functional groups in relative proximity to one another may be achieved by selecting a reagent comprising, for example, two alkyne groups joined by a linker, wherein the linker has a molecular size and/or length corresponding to the desired distance between functionalized locations on the carbon-containing molecule. In some cases, a rigid linker may be utilized, wherein the rigid linker has sufficient rigidity or steric properties that establish and maintain a sufficient distance between the functional groups when bonded to the carbon-containing molecule.

In some cases, the linker may comprise a chain, such as an alkyl or heteroalkyl chain, with the functional group or groups, or precursors thereof (e.g., alkyne, nucleophile), attached to the terminal end of the chain. In one set of embodiments, the rigid linker may comprise an aryl, heteroaryl, alkene, heteroalkene, alkyne, or heteroalkyne group. Where such rigid linkers are used, they can have lengths, or can effectively separate the functional groups or functional group precursors by lengths, at least as great as that equal to the length of the molecule:

where x is at least 2, or in other embodiments, 3, 4, 5, 6, 7, or greater. The structures above are not to be taken as limiting with respect to any type of linker that can be used, but simply as a comparative measure of the length of separation that the linker can provide, as measured on the molecular scale as would be understood by those of ordinary skill in the art. In this aspect of the invention, the linker can include one or more rigid portions and one or more non-rigid portions, so long as the combination of rigid and non-rigid portions of the linker separates the two functional groups by at least the distance noted above (as a comparative measure), even when non-rigid portions of the molecule allow the two functional groups to come into closer proximity than the distance of the rigid portion itself. As used herein, a "rigid" portion means a portion of a molecule, the ends of which are separated by a distance which cannot change (outside of normal molecule-scale changes in temperature, etc.) without breaking at least one bond. For example, a portion of a molecule including sp$^3$-hybridized carbon atoms will not be rigid (e.g., alkyl chains, and the like), while sp$^2$-hybridized or sp-hybridized carbon atoms will impart a relatively higher degree of rigidity (e.g., aryl groups, alkynyl groups). Those of ordinary of skill in the art will understand such terminology.

In some cases, the carbon-containing molecule may comprise an atom or group that may be further reacted to introduce additional groups to the molecule. Introduction of a first functional group onto the carbon-containing molecule may allow for additional functionalization of the first functional group. For example, the method may comprise reacting the carbon-containing molecule and the alkyne with a first nucleophile to form a substituted carbon-containing molecule. Subsequent reaction of the substituted carbon-containing molecule with a second nucleophile or other species (e.g., functional group precursor) may allow other functional groups to be appended to the carbon-containing molecule via, for example, a covalent bond.

For example, at least one of R$^1$, R$^2$, and R$^3$ can be replaced with a second atom or chemical group or can participate in linkage (e.g., bonding) to a second atom or chemical group. As used herein, the term "replaced" may refer to chemical reactions in which a first functional group is at least partially replaced by a second functional group as in, for example, S$_N$2 reactions. The atom or group may comprise a reactive group capable of forming a bond (e.g., covalent, non-covalent) with another atom or group. For example, the substituted carbon-containing molecule may comprise a leaving group, such that reaction with a nucleophile may replace the leaving group. Alternatively, the substituted carbon-containing molecule may comprise a nucleophile that may donate electrons to an electrophilic reagent to form a bond. In some cases, the substituted carbon-containing molecule may comprise a group that undergoes a radical reaction, a pericyclic reaction (e.g., Diels-Alder reaction, cycloaddition, etc.), a metal-catalyzed reaction (e.g., a metathesis reaction), an oxidation reaction, a reduction reaction, or any other chemical reaction known in the art. The functionalization (e.g., substitution, addition, etc.) may be performed under conditions that may be unreactive to the remainder of the compound (e.g., the carbon-containing molecule), other than R$^1$, R$^2$, or R$^3$.

In some embodiments, R$^1$, R$^2$, or R$^3$ may comprise a crosslinking group, i.e., a group capable of forming a bond with another group. For example, the crosslinking group may form a bond between the carbon-containing molecule and a polymer (e.g., via a functional group on the carbon-containing molecule), or between two polymers. The crosslinking group may comprise, for example, an acid chloride, an alkene, an alkyne, a halide, a group capable of chelating a metal, etc., and may be reacted using methods known in the art. In some cases, R$^1$, R$^2$, or R$^3$ may comprise a terminal alkene, which may be reacted via a metathesis reaction to form a bond to a terminal alkene of another molecule or group.

Figure 2:
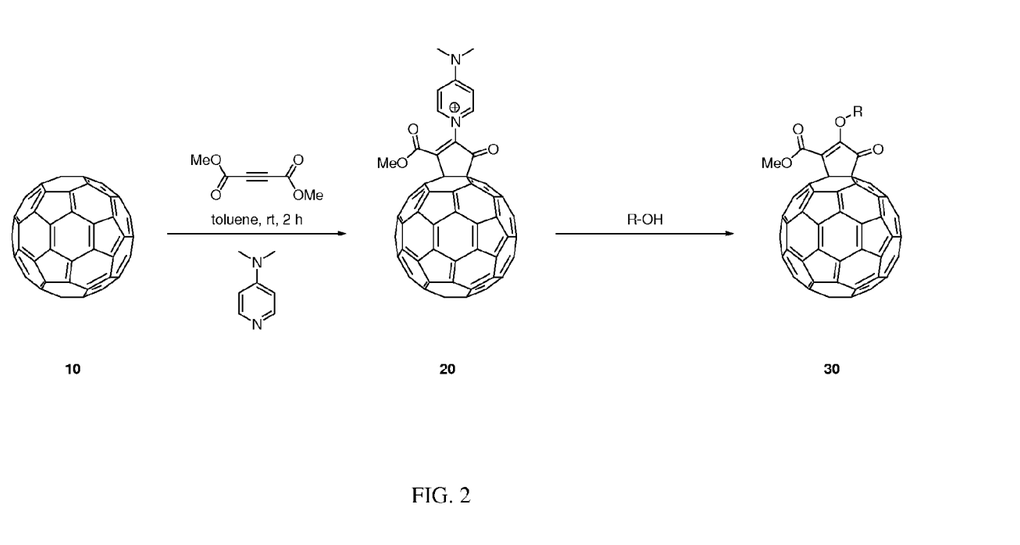
FIG. 2 shows a synthesis of a functionalized fullerene molecule, according to one embodiment of the invention.
Figure 3:
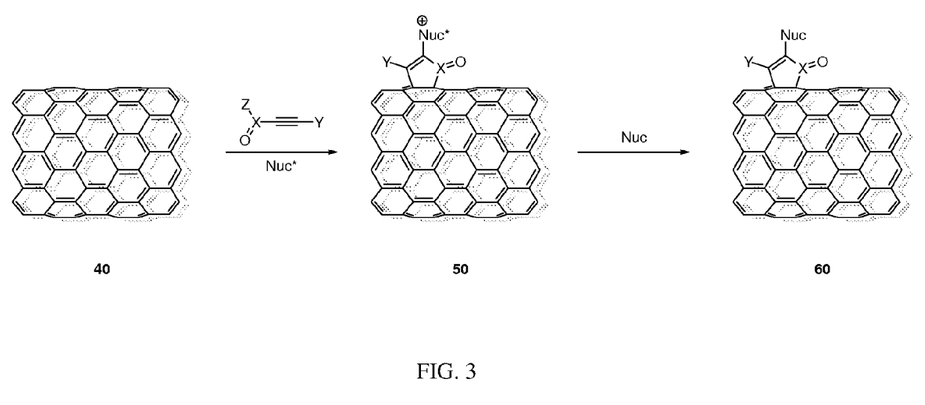
FIG. 3 shows a synthesis of a functionalized carbon nanotube, according to one embodiment of the invention.

In some embodiments, the present invention may comprise formation of a charged intermediate via reaction between a first, aprotic nucleophile, an alkyne, and a carbon-containing molecule. The charged intermediate may be a stable isolable compound, or, in some cases, the intermediate may not be isolated. The charged intermediate may be further reacted with a second, protic nucleophile, such as an alcohol, amine, thiol, enamine, enolate, etc. In some cases, the first, aprotic nucleophile may be used as a catalyst to produce the charged intermediate. In the illustrative embodiment shown in FIG. 2, $C_{60}$ may be reacted with N,N-dimethylaminopyridine (DMAP) (e.g., a first nucleophile) and dimethyl acetylenedicarboxylate (DMAD) (e.g., an alkyne) to produce substituted molecule 10, which can be further reacted with, for example, an alcohol or other species (e.g., a second nucleophile) to form substituted molecule 20. In another illustrative embodiment, carbon nanotube 40 may be reacted with a first nucleophile (e.g., "Nuc*") and an alkyne to produce a charged molecule 50, which can be further reacted with a second nucleophile (e.g., "Nuc") to afford substituted carbon nanotube 60, as shown in FIG. 3.

Methods of the invention may advantageously be performed using relatively mild conditions, compared to known methods, to form products as described herein. For example, the reaction between the alkyne, nucleophile, and carbon-containing molecule may be performed at temperatures less than 100° C., less than 80° C., less than 60° C., less than 40° C., or, in some cases, less than 30° C. In some embodiments, the reaction may be performed at room temperature. The reaction may also be performed at pressures less than 10,000 atm, less than 5000 atm, less than 1000 atm, less than 500 atm, less than 100 atm, less than 50 atm, or less than 10 atm. In some embodiments, the reaction may be performed at a pressure of about 1 atm.

In some cases, methods of the invention may be performed without need for additional reagents to enhance the reactivity of the alkyne, nucleophile, and/or carbon-containing molecule. For example, known methods may require the use of a strong acid (e.g., nitric acid) or a strong base (e.g., lithium diisopropyl amine) in order to functionalize a carbon-containing molecule. Methods of the invention may be performed in the absence of strong acids or strong bases. Those of ordinary skill in the art would be able to identify strong acids and strong bases. Examples of strong acids include, but are not limited to, nitric acid, sulfuric acid, hydrochloric acid, hydrobromic acid, and the like. Examples of strong bases include, but are not limited to, lithium diisopropyl amine (LDA), alkyl lithiums (e.g., butyl lithium), sodium amide, metal hydroxides, and the like. As used herein, a strong acid or a strong base does not refer to any component of the reaction (e.g., alkyne, nucleophile, carbon-containing molecule) which reacts to form at least a portion of the product (e.g., the substituted carbon-containing molecule). Rather, strong acids and a strong bases may refer to reagents which are utilized to activate components of the reaction and/or to enhance the reaction.

The ability to functionalize carbon-containing molecules (e.g., nonplanar carbon-containing molecules) using such mild conditions may be surprising, since known methods generally required the use of high temperatures (e.g., greater than 100° C.), high pressure, or strong acids and/or strong bases to provide sufficient reactivity.

Methods of the invention may be used to synthesize carbon-containing molecules comprising a wide range of functional groups. For example, functional groups may include peptides, proteins, DNA, RNA, peptide nucleic acids (PNA), metal complexes, ligands for metals, ligands for proteins, antibodies, polarizable aromatics, crown ethers, hydroxylamines, polymers, initiators for polymerizations, liquid crystals, fluorocarbons, synthetic receptors, and the like. In some cases, the compound may be covalently bonded to DNA, RNA, PNA, or a protein. The properties of the carbon-containing molecules may also be tailored based on the substitution of the curved portion of the fused, aromatic network. Those skilled in the art would recognize what types of functional groups would afford a particular, desired property, such as the ability to determine an analyte. In one set of embodiments, carbon-containing molecules may be functionalized with a binding site for determination of a target analyte, wherein the carbon-containing molecule may be functionalized with a binding site capable of interacting with a target analyte.

In some embodiments, the interaction between the analyte and the binding site may comprise formation of a bond, such as a covalent bond (e.g. carbon-carbon, carbon-oxygen, oxygen-silicon, sulfur-sulfur, phosphorus-nitrogen, carbon-nitrogen, metal-oxygen or other covalent bonds), an ionic bond, a hydrogen bond (e.g., between hydroxyl, amine, carboxyl, thiol and/or similar functional groups, for example), a dative bond (e.g. complexation or chelation between metal ions and monodentate or multidentate ligands), or the like. The interaction may also comprise Van der Waals interactions. In one embodiment, the interaction comprises forming a covalent bond with an analyte. The binding site may also interact with an analyte via a binding event between pairs of biological molecules. For example, the carbon-containing molecule may comprise an entity, such as biotin that specifically binds to a complementary entity, such as avidin or streptavidin, on a target analyte.

In some cases, the binding site may comprise a biological or a chemical molecule able to bind to another biological or chemical molecule in a medium (e.g., solution, vapor phase, solid phase). For example, the binding site may be a functional group, such as a thiol, aldehyde, ester, carboxylic acid, hydroxyl, or the like, wherein the functional group forms a bond with the analyte. In some cases, the binding site may be an electron-rich or electron-poor moiety within the polymer, wherein interaction between the analyte and the conducting polymer comprises an electrostatic interaction.

The binding site may also be capable of biologically binding an analyte via an interaction that occurs between pairs of biological molecules including proteins, nucleic acids, glycoproteins, carbohydrates, hormones, and the like. Specific examples include an antibody/peptide pair, an antibody/antigen pair, an antibody fragment/antigen pair, an antibody/antigen fragment pair, an antibody fragment/antigen fragment pair, an antibody/hapten pair, an enzyme/substrate pair, an enzyme/inhibitor pair, an enzyme/cofactor pair, a protein/substrate pair, a nucleic acid/nucleic acid pair, a protein/nucleic acid pair, a peptide/peptide pair, a protein/protein pair, a small molecule/protein pair, a glutathione/GST pair, an anti-GFP/GFP fusion protein pair, a Myc/Max pair, a maltose/maltose binding protein pair, a carbohydrate/protein pair, a carbohydrate derivative/protein pair, a metal binding tag/metal/chelate, a peptide tag/metal ion-metal chelate pair, a peptide/NTA pair, a lectin/carbohydrate pair, a receptor/hormone pair, a receptor/effector pair, a complementary nucleic acid/nucleic acid pair, a ligand/cell surface receptor pair, a virus/ligand pair, a Protein A/antibody pair, a Protein G/antibody pair, a Protein L/antibody pair, an Fc receptor/antibody pair, a biotin/avidin pair, a biotin/streptavidin pair, a drug/target pair, a zinc finger/nucleic acid pair, a small molecule/peptide pair, a small molecule/protein pair, a small molecule/target pair, a carbohydrate/protein pair such as maltose/MBP (maltose binding protein), a small molecule/target pair, or a metal ion/chelating agent pair.

The analyte may be a chemical or biological analyte. The term "analyte," may refer to any chemical, biochemical, or biological entity (e.g. a molecule) to be analyzed. In some cases, the polymeric structure may be selected to have high specificity for the analyte, and may be a chemical, biological, or explosives sensor, for example. In some embodiments, the analyte comprises a functional group that is capable of interacting with at least a portion of the emissive polymer material. For example, the functional group may interact with the outer layer of the article by forming a bond, such as a covalent bond. In some cases, the binding site may determine changes in pH, moisture, temperature, or the like. In one embodiment, the analyte is a biological molecule, such as a protein.

In some cases, the carbon-containing molecules may comprise a metal complex and/or a ligand for binding a metal-containing species, such as a metal (e.g., an electrocatalytic metal), metal oxide, metal alloy, or the like. For example, a metal complex, or ligand for binding a metal-containing species, may be attached to (e.g., bonded to) a carbon-containing molecule as described herein. In some cases, the metal complex may be an electrocatalytic group, i.e., a group capable of enhancing (e.g., catalyzing) an electrochemical reaction (e.g., oxidation, reduction, etc.). For example, the electrocatalytic group may useful in the reduction and/or oxidation of species including organic compounds (e.g., alcohols), oxygen, water, hydrogen, carbon dioxide, and the like. Some examples of electrocatalytic groups comprise metal atoms such as ruthenium, rhodium, osmium, iridium, palladium and platinum metal atoms. Those of ordinary skill in the art would be able to identify and select electrocatalytic groups suitable for use in the context of the invention.

In some embodiments, the carbon-containing molecule may be appropriately functionalized to impart desired characteristics (e.g., water-solubility, surface properties) to the carbon-containing molecule. For example, the carbon-containing molecule may be functionalized or derivatized to include compounds, functional groups, atoms, or materials that can alter or improve properties of the material. In some embodiments, the carbon-containing molecule may include compounds, atoms, or materials that can alter or improve properties such as compatibility with a medium (e.g., water), photo-stability, and biocompatibility. In some cases, the carbon-containing molecule may comprise functional groups selected to possess an affinity for a surface. In some embodiments, the carbon-containing molecule may be functionalized to facilitate adsorption onto a particular surface. For example, the carbon-containing molecule can be functionalized with carboxylic acid moieties, which may allow for electrostatic adsorption onto charged surfaces, such as glass surfaces, particle surfaces, and the like.

In some embodiments, the carbon-containing molecule may be functionalized to alter the compatibility of the carbon-containing molecule with respect to a fluid carrier (e.g., solvent). For example, the carbon-containing molecule may be functionalized with one or more hydrophilic groups to enhance the compatibility (e.g., solubility) of the carbon-containing molecule with aqueous solvents, such as water. That is, the carbon-containing molecules may comprise functional groups which enhance the hydrophilicity of the carbon-containing molecules. Examples of such hydrophilic groups include, but are not limited to, amines, thiols, alcohols, carboxylic acids and carboxylates, sulfates, phosphates, a polyethylene glycol (PEG) or a derivative of polyethylene glycol. Derivatives include, but are not limited to, functionalized PEGs, such as amine, thiol, and carboxyl functionalized PEG. One screening test for selection of an appropriate functional group to enhance the hydrophilcity or water-solubility of a carbon-containing molecule may involve placing a functionalized carbon-containing molecule in a fluid carrier such as water and evaluating the computability (e.g., solubility) carbon-containing molecule in the fluid carrier. Those of ordinary skill in the art would be able to evaluate whether or not the functionalized carbon-containing molecule exhibits a sufficient level of computability with a particular fluid carrier to suit a particular application.

In some cases, the functionalized carbon-containing molecule may be substantially water soluble. The term "water soluble" is used herein as it is commonly used in the art to refer to the dispersion of a species (e.g., carbon-containing molecule) in an aqueous environment. In some cases, the water soluble species may be combined with a fluid carrier to form a solution. In some cases, the water soluble species may be combined with a fluid carrier to form a dispersion or suspension. In some cases, the carbon-containing molecule may be functionalized to alter the compatibility of the carbon-containing molecule with respect to a polymeric material. For example, the carbon-containing molecule may be functionalized with groups that allow the molecules to be soluble or miscible with a polymer matrix. The functional groups may be selected to impart compatibility with a particular material. For example, the carbon-containing molecule may be functionalized with various hydrophobic groups to increase compatibility of the molecule with a hydrophobic polymer. In some cases, the carbon-containing molecule may be appropriately functionalized to be miscible with, for example, polyamides, polyesters, polyolefins, polycarbonates, polyarylethers, or the like. This may allow for the formation of polymer blends comprising carbon-containing molecules.

In some cases, the carbon-containing molecule may be covalently bound to a polymer matrix. In some cases, the carbon-containing molecule may not be covalently bound to the polymer matrix, but may be otherwise supported by (e.g., substantially contained within) or integrally connected to the polymer matrix. In some embodiments, polymers comprising carbon-containing molecules (e.g, covalently or non-covalently bonded to the polymer) may exhibit higher modulus, higher softening temperatures, or other advantageous features, when compared to an essentially identical polymer, lacking the carbon-containing molecule, under essentially identical conditions.

Compositions of the present invention may be useful in various applications including chemical sensors, transistors (e.g., organic transistors), transparent conductive coatings, electrodes (e.g., for electrocatalysis), components in photovoltaic devices, light-emitting diodes (e.g., OLEDs, PLEDs, etc.) reinforcing elements for polymers including high strength polymers, actuators (e.g., polymer mechanical actuators), circuits, and emissive elements. The compositions may also be useful as biological imaging agents and medical diagnostic agents. In some cases, the composition may be useful in cosmetic compositions. The ability to functionalize carbon-containing molecules such as fullerenes, carbon nanotubes, and graphene may aid in the formation of stable mixtures (e.g., solutions, dispersions) comprising carbon-containing molecules or in the separation of different types of carbon-containing molecules (e.g., fullerenes, carbon nanotubes).

In one set of embodiments, functionalized carbon-containing molecules (e.g., carbon nanotubes) may be useful as electron transport materials in photovoltaic devices. The functionalized carbon-containing molecules may be combined with a material such as a conducting polymer, wherein the carbon-containing molecules are substituted with groups facilitating the stable formation of polymer blends, as described herein. In operation, the polymer matrix may act as an electron donor while the carbon-containing molecules may act as the electron acceptors, wherein the carbon-containing molecules enhance the electron mobility through the device, resulting in photovoltaic devices having improved performance.

In some embodiments, functionalized carbon-containing molecules may be useful as electrocatalysts. For example, carbon-containing molecules may be functionalized with electrocatalytic groups, such as a metal complex, and may be capable of electrochemically reducing organic compounds, carbon dioxide, oxygen, and the like. For example, functionalized carbon-containing materials comprising an electrocatalytic group may be used reduce water to produce hydrogen. In some cases, functionalized carbon-containing materials comprising an electrocatalytic group that may be useful in the reduction of oxygen to produce water. In some cases, carbon dioxide may be reduced using functionalized carbon-containing materials described herein. In some cases, the functionalized carbon-containing molecules may be capable of electrochemically oxidizing organic compounds including alcohols (e.g. methanol, ethanol, etc.), water, hydrogen, and the like. For example, the functionalized carbon-containing molecules may be useful in the oxidation of water to produce oxygen, i.e., may be useful in the electrolysis of water. In some cases, the functionalized carbon-containing molecules may be useful in the oxidation of hydrogen to produce protons. In some cases, methanol may be oxidized using functionalized carbon-containing materials described herein to produce carbon dioxide and water.

Compositions of the invention may be provided as a solid or in combination with a fluid carrier. In some cases, the present invention provides a mixture comprising compositions as described herein and at least one fluid carrier. The mixture may be a solution or a dispersion, for example. In some cases, compositions of the invention may form an ionic assembly, with or without additional components. The mixtures may be useful in the separation or purification of compositions comprising nonplanar carbon-containing molecules, such as carbon nanotubes and fullerenes. In one embodiment, the mixture may be useful in the separation of carbon nanotubes.

In some embodiments, it may be desirable to remove the functional groups from the carbon-containing molecule. The functional groups as described herein may be removed (e.g., thermally removed) using relatively mild reaction conditions. That is, the bond(s) formed between the functional group(s) and the carbon-containing molecule may be broken in order to obtain the original, unsubstituted carbon-containing molecule using conditions that may be mild when compared to known methods. For example, a five-membered ring fused to a carbon-containing molecule may be thermally removed by heating at 700° C. or less, 600° C. or less, 500° C. or less, 400° C. or less, or 300° C. or less. In an illustrative embodiment, a five-membered ring comprising the structure, and fused to a carbon-containing molecule (e.g., a fullerene, a carbon nanotube) may be thermally removed from the carbon-containing molecule by exposure to temperatures in the range between 200-300° C.

As used herein, the terms "sp² hybridization" and "sp²-hybridized" are given their ordinary meaning in the art and refer to atoms (e.g., carbon atoms) which are capable of forming one double (e.g., pi) bond with another $sp^2$-hybridized atom. Atoms having $sp^2$ hybridization generally exhibit a trigonal planar bonding geometry, where the atom bears three $sp^2$-hybrid orbitals in one plane and one p orbital in a plane that is perpendicular to the three $sp^2$-hybrid orbitals. For example, carbon atoms of a phenyl ring are $sp^2$-hybridized. As used herein, the terms "$sp^3$ hybridization" and "$sp^3$-hybridized" are given their ordinary meaning in the art and refer to atoms which are capable of forming up to four single bonds with other atoms. Atoms having $sp^3$ hybridization generally exhibit a substantially tetrahedral bonding geometry. For example, carbon atoms of an ethyl group are $sp^3$-hybridized. Those of ordinary skill in the art would understand the meaning of such terms, and would be able to identify the hybridization of atoms in a molecule.

Alkynes suitable for use in the invention include any species comprising a triple bond, such as a carbon-carbon triple bond. The alkyne may be selected to be an electrophilic species, e.g., a species able to accept electrons from, for example, a nucleophile. Those of ordinary skill in the art would be able to select appropriate alkynes for use in the invention. For example, the alkyne may be an electron-poor or electron-deficient alkyne. In some cases, electron-deficient alkynes may have increased reactivity or may be activated towards nucleophilic attack or other reactions. The alkyne may be substituted with at least one electron-withdrawing group, such as a carbonyl group, sulfonate, or phosphonate, aryl group (e.g., an aryl group substituted with electron-deficient groups), halide (e.g., iodide, bromide, chloride, fluoride), nitrile, nitro group, amide, or the like. In some cases, the alkyne comprises a halogenated alkyl group, such as trifluoromethyl or perfluoroalkyl.

The alkyne may also be selected to have an appropriate steric size to enable interaction (e.g., reaction) with the nucleophile and carbon-containing molecule to form compounds as described herein. For example, some sterically large groups may hinder reaction of the alkyne with the nucleophile and carbon-containing molecule due to steric crowding. Those of ordinary skill in the art would be able to select which alkynes may be suitable for use in the invention.

As used herein, the term "nucleophile" is given its ordinary meaning in the art and refers to a chemical moiety having a reactive pair of electrons. A nucleophile may include any species capable of donating electrons, generally resulting in formation of a bond, such as a covalent bond. The nucleophile may comprise, for example, a heteroatom such as oxygen, nitrogen, or phosphorous, or other atoms capable of donating electrons to form a bond. In some cases, the nucleophile may comprise an electron-donating group, such as amino, alkoxy (e.g., methoxy), heteroaryl, and the like. In some cases, the nucleophile may comprise a heteroalkyl or heteroaryl group, optionally substituted. For example, the nucleophile may be $N(R^6)_3$, $P(R^6)_3$, $O(R^6)_2$, $S(R^6)_2$, pyridine, pyrrole, thiophene, furan, or substituted derivatives thereof, wherein $R^6$ is halide, hydroxy, alkyl, heteroalkyl, alkenyl, heteroalkenyl, alkynyl, heteroalkynyl, aryl, heteroaryl, or a salt thereof, optionally substituted.

Examples of nucleophiles include uncharged compounds such as water, amines, mercaptans and alcohols, and charged moieties such as alkoxides, thiolates, carbanions, and a variety of organic and inorganic anions. Some specific examples of uncharged nucleophiles include N,N-dimethylaminopyridine and imidazole. Some specific examples of anionic nucleophiles include anions such as hydride, hydroxide, azide, cyanide, thiocyanate, acetate, formate or chloroformate, and bisulfite. In some cases, the nucleophile may comprise a carbanion species, including organometallic reagents such as organocuprates, organozincs, organolithiums, Grignard reagents, enolates, acetylides, and the like. In some embodiments, the nucleophile may be N,N-dimethylaminopyridine. In some embodiments, the nucleophile may be imidazole.

Some methods of the invention may comprise reacting the carbon-containing molecule with a nucleophile, wherein the nucleophile has a conjugate acid having a $pK_a$ more positive than 5.0. As used herein, a "conjugate acid" of a nucleophile refers to a protonated derivative of a nucleophile. In some cases, the conjugate acid may be a charged or an uncharged molecule. For example, when the nucleophile is imidazole, the $pK_a$ value of the conjugate acid of imidazole may refer to the $pK_a$ value of the corresponding imidazolium salt. In some cases, methods of the invention may comprise reacting the carbon-containing molecule with a nucleophile, wherein the nucleophile has a conjugate acid having a $pK_a$ more positive than 10.0, 15.0, 20.0, or, in some cases, more positive than 25.0.

Those of ordinary skill in the art would be able to select which reaction components (e.g., carbon-containing molecule, alkyne, nucleophile, etc.) would be suitable for use in the invention. Because methods of the invention may be performed rapidly and with relative ease, a simple screening test may involve performing a series of reactions in which one or more of the components may be varied. For example, reactions may be performed using a carbon nanotube, the same nucleophile, and a series of alkynes varying in steric size and electronic properties to determine which alkynes may be suitable for use in the invention.

Solvents suitable for used in methods of the invention include organic solvents, non-organic solvents (e.g., aqueous solvents), or combinations thereof. In some cases, the solvent may be a polar solvent or a non-polar solvent. The solvent may be selected for its compatibility with the carbon-containing molecules or other components of the reaction as described herein. For example, the solvent may be selected such that the carbon-containing molecule is substantially soluble in the solvent. Compatibility does not necessarily require solubility, and solvents capable of forming a stable suspension, colloid, or other mixture known to the art, with the carbon-containing molecule or other component may be sufficiently compatible for use in the invention. Various solvents may be used in the context of the invention, so long as each solvent is sufficiently compatible with the respective component. The solvents may also be useful as fluid carriers, for example, to form mixtures comprising the compositions described herein.

In some cases, the solvent may be selected to be sufficiently polar to provide stability for ionic species within the reaction (e.g., Zwitterions) as well as sufficiently non-polar such that the ionic species may participate in the reaction. Examples of some organic solvents include, but are not limited to, hexane, cyclohexane, pentane, benzene, toluene, and other hydrocarbons, ethers, dichloromethane, chloroform, carbon tetrachloride, 1,2,4-trichlorobenzene, carbon disulfide, tetrahydrofuran (THF), N,N-dimethylformamide (DMF), ethyl methyl ketone, acetone, N-methylpyrrolidinone, acetonitrile, methanol, other alcohols, and the like. In some cases, the carrier fluid is an aqueous solvent or other solvent that is miscible with an aqueous solvent. In some cases, the solvent may be THF, DMF, or toluene.

EXAMPLES

The following general procedures were followed in the context of methods of the invention. Raw (HiPCO) SWCNTs, received from Carbon Nanotechnologies Inc. (CNI lot# R0204), were further purified by exposure to air at 300° C. followed by washing with concentrated HCl to remove remaining metal catalysts before use. Fullerenes (99.5%) were obtained from Alfa Aesar and used as received. All solvents used were of spectroscopic grade unless otherwise noted. Anhydrous toluene, dichloromethane, acetonitrile, and tetrahydrofuran were obtained using a solvent purification system (Innovative Technologies). All other chemicals were of reagent grade and used as received.

Nuclear Magnetic Resonance (NMR) spectra were recorded on Inova-500 NMR Spectrometer. Chemical shifts are referenced to residual solvent. High-Resolution Mass Spectra (HRMS) were obtained on Bruker Daltonics APEX II 3 Telsa FTICR-MS. Raman spectra were measured on a Kaiser Hololab 5000R Raman Spectrometer using the excitation wavelength of 785 nm. The spectra in the UV-Vis-NIR range were obtained using a Cary 6000i UV-vis-NIR spectrometer. Thermogravimetric analyses (TGA) were performed with a TGA Q50 apparatus (TA instruments). Experiments were carried out under nitrogen. The samples were heated at 5° C./min from 22° C. to 800° C. X-ray crystallographic data was collected on a Siemens Platform three-circle diffractometer coupled to a Bruker-AXS Smart Apex CCD detector. All synthetic manipulations were carried out under an argon atmosphere using standard Schlenk techniques unless otherwise noted. Glassware was oven-baked and cooled under $N_2$ atmosphere.

Example 1

Functionalized fullerenes were synthesized according to the following general procedure, with N,N-dimethylaminopyridine (DMAP) as the nucleophile and dimethyl acetylenedicarboxylate (DMAD) as the alkyne, to obtain a vinyl methoxy fullerene analog. A mixture of $C_{60}$ (10 mg, 0.014 mmol) and DMAP (4.4 mg, 0.036 mmol) in toluene in a 25-mL Schlenk tube was sonicated using an ultrasonic bath (Branson 2510, 20 W, 42 kHz) until a homogeneous violet solution was obtained. To the resulting mixture was injected a solution of DMAD (3.4 μL, 0.028 mmol) in toluene (0.5 mL) dropwise. After addition of DMAD was complete, the system was stirred at room temperature for 0.5 h followed by the addition of methanol (0.5 mL). The resulting mixture was further stirred for another 2 h. The solution was concentrated and the residue was subjected to column chromatography. The product was obtained as a red solid (8.1 mg, 68%). Some fullerene starting material was also recovered (1.9 mg, 19%).

Example 2

A vinyl 2-methoxyethyloxy fullerene analog was synthesized using the following procedure, with N,N-dimethylaminopyridine (DMAP) as the first nucleophile, dimethyl acetylenedicarboxylate (DMAD) as the alkyne, and 2-methoxyethanol as the second nucleophile, to obtain the product. A mixture of $C_{60}$ (10 mg, 0.014 mmol) and DMAP (4.4 mg, 0.036 mmol) in toluene in a 25-mL Schlenk tube was sonicated using an ultrasonic bath until a homogeneous violet solution was obtained. To the resulting mixture was injected a solution of DMAD (3.4 μL, 0.028 mmol) in toluene (0.5 mL) dropwise. After addition, the system was stirred at room temperature for 0.5 h followed by the addition of 2-methoxyethanol (0.5 mL). The resulting mixture was further stirred for another 2 h. The solution was concentrated and the residue was subjected to column chromatography. The product was obtained as a red solid (7.7 mg, 62%). Some fullerene starting material was also recovered (2.1 mg, 21%).

Example 3

A single-walled carbon nanotube (SWCNT) analog was synthesized using the following procedure, with DMAP as the nucleophile, DMAD as the alkyne, and 2-methoxyethanol as the second nucleophile, to obtain the product. A suspension of purified SWCNTs (4.0 mg, 0.33 mmol of carbon) in THF (40 mL) was sonicated for 3 min using an ultrasonic probe (Branson Sonifier 450, 60 W, 20 kHz). The heterogeneous solution was heated at 60° C. To the SWCNT suspension were added simultaneously a solution of DMAD (0.51 mL, 4.2 mmol) in THF (10 mL) and a solution of DMAP (0.51 g, 4.2 mmol) in THF (10 mL) via syringe pump within 40 h. (In cases where a second nucleophile is required to obtain the product, the second nucleophile may be added after the addition of DMAD and DMAP completed, and the mixture may be stirred at 60° C. for another 12 h.) The reaction mixture was centrifuged at 5000 rpm for 5 min. The supernatant was discarded and the residue was dispersed in DMF for 5 min using an ultrasonic bath. The mixture was centrifuged (5000 rpm, 5 min) and the supernatant was discarded. The same sequence was repeated twice with DMF and acetone used as solvents to produce functionalized SWCNTs, which were dried under vacuum overnight.

Definitions

For convenience, certain terms employed in the specification, examples, and appended claims are listed here.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. The alkyl groups may be optionally substituted, as described more fully below. Examples of alkyl groups include, but are not limited to, methyl, ethyl, propyl, isopropyl, butyl, isobutyl, tert-butyl, 2-ethylhexyl, cyclopropyl, cyclobutyl, cyclopentyl, cyclohexyl, and the like. "Heteroalkyl" groups are alkyl groups wherein at least one atom is a heteroatom (e.g., oxygen, sulfur, nitrogen, phosphorus, etc.), with the remainder of the atoms being carbon atoms. Examples of heteroalkyl groups include, but are not limited to, alkoxy, poly(ethylene glycol)-, alkyl-substituted amino, tetrahydrofuranyl, piperidinyl, morpholinyl, etc.

The terms "alkenyl" and "alkynyl" refer to unsaturated aliphatic groups analogous to the alkyl groups described above, but containing at least one double or triple bond respectively. The "heteroalkenyl" and "heteroalkynyl" refer to alkenyl and alkynyl groups as described herein in which one or more atoms is a heteroatom (e.g., oxygen, nitrogen, sulfur, and the like).

The term "aryl" refers to an aromatic carbocyclic group having a single ring (e.g., phenyl), multiple rings (e.g., biphenyl), or multiple fused rings in which at least one is aromatic (e.g., 1,2,3,4-tetrahydronaphthyl, naphthyl, anthryl, or phenanthryl), all optionally substituted. "Heteroaryl" groups are aryl groups wherein at least one ring atom in the aromatic ring is a heteroatom, with the remainder of the ring atoms being carbon atoms. Examples of heteroaryl groups include furanyl, thienyl, pyridyl, pyrrolyl, N-lower alkyl pyrrolyl, pyridyl-N-oxide, pyrimidyl, pyrazinyl, imidazolyl, indolyl and the like, all optionally substituted.

The terms "amine" and "amino" refer to both unsubstituted and substituted amines, e.g., a moiety that can be represented by the general formula: N(R')(R'')(R''') wherein R', R'', and R''' each independently represent a group permitted by the rules of valence.

The terms "acyl," "carboxyl group," or "carbonyl group" are recognized in the art and can include such moieties as can be represented by the general formula:

wherein W is H, OH, O-alkyl, O-alkenyl, or a salt thereof. Where W is O-alkyl, the formula represents an "ester." Where W is OH, the formula represents a "carboxylic acid." In general, where the oxygen atom of the above formula is replaced by sulfur, the formula represents a "thiolcarbonyl" group. Where W is a S-alkyl, the formula represents a "thiolester." Where W is SH, the formula represents a "thiolcarboxylic acid." On the other hand, where W is alkyl, the above formula represents a "ketone" group. Where W is hydrogen, the above formula represents an "aldehyde" group.

As used herein, the term "substituted" is contemplated to include all permissible substituents of organic compounds, "permissible" being in the context of the chemical rules of valence known to those of ordinary skill in the art. In some cases, "substituted" may generally refer to replacement of a hydrogen with a substituent as described herein. However, "substituted," as used herein, does not encompass replacement and/or alteration of a key functional group by which a molecule is identified, e.g., such that the "substituted" functional group becomes, through substitution, a different functional group. For example, a "substituted phenyl" must still comprise the phenyl moiety and can not be modified by substitution, in this definition, to become, e.g., a heteroaryl group such as pyridine. In a broad aspect, the permissible substituents include acyclic and cyclic, branched and unbranched, carbocyclic and heterocyclic, aromatic and non-aromatic substituents of organic compounds. Illustrative substituents include, for example, those described herein. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms. This invention is not intended to be limited in any manner by the permissible substituents of organic compounds.

Examples of substituents include, but are not limited to, alkyl, aryl, aralkyl, cyclic alkyl, heterocycloalkyl, hydroxy, alkoxy, aryloxy, perhaloalkoxy, aralkoxy, heteroaryl, heteroaryloxy, heteroarylalkyl, heteroaralkoxy, azido, amino, halogen, alkylthio, oxo, acylalkyl, carboxy esters, carboxyl, carboxamido, nitro, acyloxy, aminoalkyl, alkylaminoaryl, alkylaryl, alkylaminoalkyl, alkoxyaryl, arylamino, aralkylamino, alkylsulfonyl, carboxamidoalkylaryl, carboxamidoaryl, hydroxyalkyl, haloalkyl, alkylaminoalkylcarboxy, aminocarboxamidoalkyl, alkoxyalkyl, perhaloalkyl, arylalkyloxyalkyl, and the like.

The term "electron-donating group," as used herein, refers to a functionality which draws electrons to itself less than a hydrogen atom would at the same position. Exemplary electron-donating groups include amino, methoxy, and the like.

The term "electron-withdrawing group" is recognized in the art and as used herein means a functionality which draws electrons to itself more than a hydrogen atom would at the same position. Exemplary electron-withdrawing groups include nitro, cyano, carbonyl groups (e.g., aldehydes, ketones, esters, etc.), sulfonyl, trifluoromethyl, and the like.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed:

1. A composition, comprising:
a compound or salt thereof having the formula, wherein:
A is a carbon-containing molecule comprising a nonplanar aromatic portion comprising a fused network of aromatic rings;
$R^1$ has the structure, wherein X is H, OH, halide, alkyl, heteroalkyl, alkenyl, heteroalkenyl, alkynyl, heteroalkynyl, aryl, heteroaryl, or salt thereof, optionally substituted;
$R^2$ is an aryloxy group substituted with an electron-withdrawing group; and
$R^3$ is =O, =S, or =$NR^4$, wherein $R^4$ is alkyl; and
=== is a single bond or double bond.

2. A composition as in claim 1, wherein $R^2$ is

3. A composition as in claim 1, wherein the carbon-containing molecule is a fullerene.

4. A composition as in claim 1, wherein the carbon-containing molecule is a carbon nanotube.

5. A composition as in claim 1, wherein the carbon-containing molecule is a single-walled carbon nanotube.

6. A composition as in claim 1, wherein the carbon-containing molecule is a multi-walled carbon nanotube.

* * * * *